(12) United States Patent
Gupta et al.

(10) Patent No.: US 8,361,765 B2
(45) Date of Patent: Jan. 29, 2013

(54) ENZYMIC METHOD FOR THE ENANTIOSELECTIVE REDUCTION OF KETO COMPOUNDS

(75) Inventors: Antje Gupta, Wiesbaden (DE); Klaus Breese, Halle (DE); Gert Bange, Heidelberg (DE); Peter Neubauer, Oulu (FI)

(73) Assignee: IEP GmbH, Wiesbaden (DE)

( * ) Notice: Subject to any disclaimer, the term of this patent is extended or adjusted under 35 U.S.C. 154(b) by 1289 days.

(21) Appl. No.: 11/820,418

(22) Filed: Jun. 19, 2007

(65) Prior Publication Data

US 2009/0017510 A1   Jan. 15, 2009

Related U.S. Application Data

(63) Continuation of application No. 10/475,150, filed as application No. PCT/EP02/04143 on Apr. 15, 2002, now abandoned.

(30) Foreign Application Priority Data

Apr. 20, 2001 (DE) ................... 101 19 274

(51) Int. Cl.
*C12P 7/02* (2006.01)
(52) U.S. Cl. ............................ 435/155; 435/41; 435/189
(58) Field of Classification Search ............... 435/41, 435/155, 189
See application file for complete search history.

(56) References Cited

U.S. PATENT DOCUMENTS 5,342,767 A   8/1994   Wong et al.

FOREIGN PATENT DOCUMENTS

| DE | 40 14 573 C1 | 10/1991 |
| DE | 196 10 984 A1 | 9/1997 |
| EP | 0 796 914 A2 | 9/1997 |
| WO | WO 9638577 A1 | 12/1996 |

OTHER PUBLICATIONS

Aldrich Catalog (1996-1997) p. 144.*
Hummel Werner "New Alcohol Dehydrogenases for the Synthesis of Chiral Compounds" Advances in Biochemical Engineering Biotechnology, Springer, Berlin, Germany vol. 58, 1997, pp. 145-184.
Brandshaw C W et al. "Enzymatic Synthesis of (R) and (S) 1-Deuterohexanol" Applied Biochemistry and Biotechnology, Clifton, NJ, US vol. 33, 1992, pp. 15-24.
Bruce L J et al. "Solvent Selection Strategies for Extractive Biocatalysis" Biotechnology Progress vol. 7, 1991, pp. 1116-1124.
Jonsson Asa et al. "Thermodynamic and kinetic aspects on water vs. organic solvent as reaction media in the enzyme-catalysed reduction of ketones" Biochimica et biophysica Acta vol. 1430, No. 2, 1999, pp. 313-322.
Hummel Werner "Large-scale applications of NAD (P)-dependent oxidoreductases: Recent developments" Trends in Biotechnology vol. 17, No. 12, 1999, pp. 487-492.

* cited by examiner

*Primary Examiner* — Susan Hanley
(74) *Attorney, Agent, or Firm* — ProPat, L.L.C.

(57) ABSTRACT

The invention relates to an enzymatic method for the enantioselective reduction of organic keto compounds to the corresponding chiral hydroxy compounds, an alcohol dehydrogenase from *Lactobacillus minor* and a method for the enantioselective production of (S)-hydroxy compounds from a racemate.

22 Claims, No Drawings

SEQUENCE LISTING

```
<160> NUMBER OF SEQ ID NOS: 4

<210> SEQ ID NO 1
<211> LENGTH: 795
<212> TYPE: DNA
<213> ORGANISM: Artificial Sequence
<220> FEATURE:
<223> OTHER INFORMATION: Description of Artificial Sequence: DNA primer

<400> SEQUENCE: 1
atgagaggat cgcatcacca tcaccatcac ggatccatga ccgatcggtt gaaggggaaa      60
gtagcaattg taactggcgg taccttggga attggcttgg caatcgctga taagtttgtt     120
gaagaaggcg caaaggttgt tattaccggc cgtcacgctg atgtaggtga aaaagctgcc     180
agatcaatcg gcggcacaga cgttatccgt tttgtccaac acgatgcttc tgatgaaacc     240
ggctggacta agttgtttga tacgactgaa gaagcatttg gcccagttac cacggttgtc     300
aacaatgccg gaattgcggt cagcaagagt gttgaagata ccacaactga agaatggcgc     360
aagctgctct cagttaactt ggatggtgtc ttcttcggta cccgtcttgg aatccaacgt     420
atgaagaata aaggactcgg agcatcaatc atcaatatgt catctatcga aggttttgtt     480
ggtgatccag ctctgggtgc atacaacgct tcaaaaggtg ctgtcagaat tatgtctaaa     540
tcagctgcct tggattgcgc tttgaaggac tacgatgttc gggttaacac tgttcatcca     600
ggttatatca agacaccatt ggttgacgat cttgaagggg cagaagaaat gatgtcacag     660
cggaccaaga caccaatggg tcatatcggt gaacctaacg atatcgcttg gatctgtgtt     720
tacctggcat ctgacgaatc taaatttgcc actggtgcag aattcgttgt cgacggaggg     780
tacaccgccc aatag                                                      795

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: DNA primer
<220> FEATURE:
<221> NAME/KEY: misc_feature
<222> LOCATION: (14)..(35)
<223> OTHER INFORMATION: n = a, t, c or g
      n pos. 14, 20, 29, 35

<400> SEQUENCE: 2
```

```
gcggatccat gacngaycgn ttraarggna argtngc                                37
```

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: DNA primer
<220> FEATURE:
<221> NAME/KEY: misc_feature
<222> LOCATION: (16)..(34)
<223> OTHER INFORMATION: n = a, t, c or g
      n pos. 16, 19, 25, 28, 34

<400> SEQUENCE: 3

```
gggaagcttc taytgngcng trtanccncc rtcnac                                 36
```

<210> SEQ ID NO 4
<211> LENGTH: 264
<212> TYPE: PRT
<213> ORGANISM: Lactobacillus sp.

<400> SEQUENCE: 4

```
Met Arg Gly Ser His His His His His His Gly Ser Met Thr Asp Arg
  1               5                  10                  15

Leu Lys Gly Lys Val Ala Ile Val Thr Gly Gly Thr Leu Gly Ile Gly
             20                  25                  30

Leu Ala Ile Ala Asp Lys Phe Val Glu Glu Gly Ala Lys Val Val Ile
         35                  40                  45

Thr Gly Arg His Ala Asp Val Gly Glu Lys Ala Ala Arg Ser Ile Gly
     50                  55                  60

Gly Thr Asp Val Ile Arg Phe Val Gln His Asp Ala Ser Asp Glu Thr
 65                  70                  75                  80

Gly Trp Thr Lys Leu Phe Asp Thr Thr Glu Glu Ala Phe Gly Pro Val
                 85                  90                  95

Thr Thr Val Val Asn Asn Ala Gly Ile Ala Val Ser Lys Ser Val Glu
            100                 105                 110

Asp Thr Thr Thr Glu Glu Trp Arg Lys Leu Leu Ser Val Asn Leu Asp
        115                 120                 125

Gly Val Phe Phe Gly Thr Arg Leu Gly Ile Gln Arg Met Lys Asn Lys
    130                 135                 140

Gly Leu Gly Ala Ser Ile Ile Asn Met Ser Ser Ile Glu Gly Glu Val
145                 150                 155                 160

Gly Asp Pro Ala Leu Gly Ala Tyr Asn Ala Ser Lys Gly Ala Val Arg
                165                 170                 175

Ile Met Ser Lys Ser Ala Ala Leu Asp Cys Ala Leu Lys Asp Tyr Asp
            180                 185                 190

Val Arg Val Asn Thr Val His Pro Gly Tyr Ile Lys Thr Pro Leu Val
        195                 200                 205

Asp Asp Leu Glu Gly Ala Glu Glu Met Met Ser Gln Arg Thr Lys Thr
    210                 215                 220

Pro Met Gly His Ile Gly Glu Pro Asn Asp Ile Ala Trp Ile Cys Val
225                 230                 235                 240

Tyr Leu Ala Ser Asp Glu Ser Lys Phe Ala Thr Gly Ala Glu Phe Val
                245                 250                 255

Val Asp Gly Gly Tyr Thr Ala Gln
            260
```

ENZYMIC METHOD FOR THE ENANTIOSELECTIVE REDUCTION OF KETO COMPOUNDS

CROSS-REFERENCE TO RELATED APPLICATIONS

This application is a continuation of co-pending U.S. application Ser. No. 10/475,150 assigned a filing date of Jan. 12, 2004, now abandoned, which is hereby incorporated by reference in its entirety. This application further claims priority to its parent, German patent application no. 101 19 274.6 filed Apr. 20, 2001, and PCT/EP02/04143 filed Apr. 15, 2002, which are both hereby incorporated by reference herein in their entirety.

FIELD OF THE INVENTION

The present invention relates to an enzymic method for the enantioselective reduction of organic keto compounds to give the corresponding chiral hydroxy compounds, to an alcohol dehydrogenase from *Lactobacillus minor* and to an enzymic method for enantioselectively obtaining (S)-hydroxy compound from a racemate.

BACKGROUND OF THE INVENTION

Optically active hydroxy compounds are valuable synthetic building blocks for the preparation of a multiplicity of pharmacologically important compounds. These compounds are often difficult to prepare by conventional chemical methods and only rarely attain the enantiomeric purity required for pharmacological applications. Therefore, biotechnological methods are usually employed in preparing chiral compounds, the stereoselective reaction being carried out either by whole microorganisms or using isolated enzymes.

The use of isolated enzymes has often proved advantageous here, since higher yields and a higher enantiomeric purity are usually attainable by using such enzymes.

Dehydrogenases and in particular alcohol dehydrogenases are valuable catalysts for obtaining chiral products by stereoselective reduction of organic keto compounds to the corresponding chiral alcohols. Known enzymes are essentially the corresponding enzymes from yeast, equine liver or *Thermoanaerobium brockii*. These enzymes require NADH (nicotine adenine dinucleotide) or NADPH (nicotine adenine dinucleotide phosphate) as coenzyme. Other examples of known alcohol dehydrogenases are an (S)-specific alcohol dehydrogenase from *Rhodococcus erythropolis* and an (R)-specific alcohol dehydrogenase from the genus *Lactobacillus*. Both enzyme types have a broad spectrum of keto compound substrates and have high enantioselectivity. The alcohol dehydrogenases from *Lactobacillus kefir* (DE 40 14 573) and *Lactobacillus brevis* (DE 196 10 984) are particularly suitable for obtaining chiral (R)-alcohols.

However, the disadvantages of employing alcohol dehydrogenases are the low enzyme stability and enzyme activity of alcohol dehydrogenases in organic solvents and the frequently only poor water solubility of the keto compounds to be reduced. Another limiting factor for employing alcohol dehydrogenases in organic solvents is furthermore the necessary use of NADP or NAD as cofactor requirement, since the cofactor (NADP, NAD) is water-soluble and is regenerated by economical methods.

It is the object of the invention to improve said disadvantages by modifying the method conditions. This object is achieved according to the invention by using a two-phase system comprising an organic solvent, alcohol dehydrogenase, water, cofactor and keto compound.

The method of the invention has a long stability time due to the enzyme-stabilizing action of the solvent, an enantiomeric purity of more than 99.9% of the prepared chiral hydroxy compounds and a high yield based on the amount of keto compound used.

BRIEF DESCRIPTION OF THE INVENTION

The method of the invention therefore relates to a method for the enantioselective reduction of a keto compound of the formula I

$$R^1-C(O)-R^2 \qquad (I)$$

where $R^1$ and $R^2$ are, independently of one another, identical or different and are hydrogen,
1. $-(C_1-C_{20})$-alkyl in which alkyl is straight-chained or branched,
2. $-(C_2-C_{20})$-alkenyl in which alkenyl is straight-chained or branched and, optionally, comprises one, two, three or four double bonds,
4. $-(C_2-C_{20})$-alkynyl in which alkynyl is straight-chained or branched and, optionally, comprises one, two, three or four triple bonds,
5. $-(C_6-C_{14})$-aryl,
6. $-(C_1-C_8)$-alkyl-$(C_6-C_{14})$-aryl or
7. $R^1$ and $R^2$ form in combination with the $-C(O)$ radical a $-(C_6-C_{14})$-aryl or a $-(C_5-C_{14})$-heterocycle,
   where the radicals defined above under 1. to 7. are unsubstituted or, independently of one another, mono- to trisubstituted by
   a) $-OH$,
   b) halogen such as fluorine, chlorine, bromine or iodine,
   c) $-NO_2$,
   d) $-C(O)-O-(C_1-C_{20})$-alkyl in which alkyl is linear or branched and unsubstituted or mono- to trisubstituted by halogen, hydroxyl, amino or nitro, or
   e) $-(C_5-C_{14})$-heterocycle which is unsubstituted or mono- to trisubstituted by halogen, hydroxyl, amino or nitro, characterized in that
a) the compound of the formula I, alcohol dehydrogenase, water, cofactor and an organic solvent having a logP of from 0.5 to 4.0 are incubated
b) in a two-phase system and
c) the chiral hydroxy compound is isolated.

DETAILED DESCRIPTION OF THE INVENTION

Carbon atoms in the ring. Examples of $-(C_6-C_{14})$-aryl radicals are phenyl, naphthyl. The term aryl means aromatic carbon radicals having from 6 to 14, for example 1-naphthyl, 2-naphthyl, biphenylyl, for example 2-biphenylyl, 3-biphenylyl and 4-biphenylyl, anthryl or fluorenyl. Preferred aryl radicals are biphenylyl radicals, naphthyl radicals and in particular phenyl radicals. The term "halogen" means an element of the series fluorine, chlorine, bromine or iodine. The term "$-(C_1-C_{20})$-alkyl" means a hydrocarbon radical whose carbon chain is straight-chained or branched and comprises from 1 to 20 carbon atoms.

The term "$-(C_5-C_{14})$-heterocycle" represents a monocyclic or bicyclic 5-membered to 14-membered heterocyclic ring which is partially or completely saturated. Examples of heteroatoms are N, O and S. Examples of the terms $-(C_5-C_{14})$-heterocycle are radicals derived from pyrrole, furan, thiophene, imidazole, pyrazole, oxazole, isoxazole, thiazole, isothiazole, tetrazole, 1,2,3,5-oxathiadiazole 2-oxides, triazolones, oxadiazolones, isoxazolones, oxadiazolidinediones, triazoles, which are substituted by F, —CN, —CF$_3$ or —C(O)—O—(C$_1$-C$_4$)-alkyl, 3-hydroxypyrro-2,4-diones, 5-oxo-1,2,4-thiadiazoles, pyridine, pyrazine, pyrimidine, indole, isoindole, indazole, phthalazine, quinoline, isoquinoline, quinoxaline, quinazoline, cinnoline, carboline and benzo-fused, cyclopenta-, cyclohexa- or cyclohepta-fused derivatives of these heterocycles. Particular preference is given to the radicals 2- or 3-pyrrolyl, phenylpyrrolyl such as 4- or 5-phenyl-2-pyrrolyl, 2-furyl, 2-thienyl, 4-imidazolyl, methylimidazolyl, for example 1-methyl-2-, -4- or -5-imidazolyl, 1,3-thiazol-2-yl, 2-pyridyl, 3-pyridyl, 4-pyridyl, 2-, 3- or 4-pyridyl N-oxide, 2-pyrazinyl, 2-, 4- or 5-pyrimidinyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl or dihydropyridinyl, pyrrolidinyl, for example 2- or 3-(N-methylpyrrolidinyl), piperazinyl, morpholinyl, thiomorpholinyl, tetrahydrothienyl or benzodioxolanyl.

Preferred compounds of the formula I are ethyl 4-chloro-3-oxo-butanoate, acetophenone, methyl acetoacetate, ethyl 2-oxo-4-phenylbutyrate, 2,5-hexanedione, ethyl pyruvate and 2-octanone, preferably ethyl 4-chloro-3-oxobutanoate. The compounds of the formula I are used in the method of the invention in an amount of from 2% to 30%, based on the total volume, preferably from 10% to 25%, in particular from 15% to 22%.

Preference is given to adding to the water a buffer, for example potassium phosphate buffer, Tris/HCl buffer or triethanolamine buffer, having a pH of from 5 to 10, preferably a pH of from 6 to 9. The buffer concentration is from 10 mM to 150 mM, preferably from 90 mM to 110 mM, in particular 100 mM. The buffer additionally also contains magnesium ions, for example MgCl$_2$, at a concentration of from 0.2 mM to 10 mM, preferably from 0.5 to 2 mM, in particular 1 mM.

The temperature is, for example, from about 10° C. to 70° C., preferably from 30° C. to 60° C.

The organic solvents that can be used according to the invention preferably have a logP of from 0.6 to 2.0, in particular from 0.6 to 1.9, particularly preferably from 0.63 to 1.75. Examples of preferred organic solvents are diethyl ether, tert-butyl methyl ether, diisopropyl ether, dibutyl ether and ethyl acetate, in particular ethyl acetate. Ethyl acetate may be used, for example, in an amount of from 1% to 90%, based on the total volume of the reaction mixture, preferably from 15% to 60%, in particular from 20% to 50%.

The ratio of organic solvent to water is from 9 to 1 to 1 to 9, preferably from 1 to 1 to 1 to 3.

One liquid phase of the two-phase system of the invention is water and the second liquid phase is the organic solvent. Optionally, there may also still be a solid or another liquid phase produced, for example, by incompletely dissolved alcohol dehydrogenase or by the compound of the formula I. Preference, however, is given to two liquid phases without solid phase. The two liquid phases are preferably mixed mechanically so as to generate large surfaces between the two liquid phases.

The concentration of the NADPH or NADH cofactor, based on the aqueous phase, is from 0.05 mM to 0.25 mM, in particular from 0.06 mM to 0.2 mM.

Preference is given to using in the method of the invention also another stabilizer of alcohol dehydrogenase. Examples of suitable stabilizers are glycerol, sorbitol or dimethyl sulfoxide (DMSO).

The amount of glycerol is from 5% to 30%, based on the volume of the total mixture. Preferred amounts of glycerol are from 10% to 20%, in particular 20%.

It is possible to add in the method of the invention additionally isopropanol in order to regenerate the NADH or NADPH consumed. For example, alcohol dehydrogenase converts the isopropanol and NADP to NADPH and acetone.

The amount of isopropanol used is from 5% to 30%, based on the volume of the total mixture. Preferred amounts of isopropanol are from 10% to 20%, in particular 10%.

Examples of suitable alcohol dehydrogenases are derived from yeast, equine liver or *Rhodococcus erythropolis*, said enzymes requiring NADH as coenzyme, or from *Thermoanaerobium brockii, Lactobacillus kefir* or *Lactobacillus brevis*, the latter enzymes requiring NADPH as coenzyme.

If, for example, an alcohol dehydrogenases of yeast, equine liver, *Thermoanaerobium brockii* or *Rhodococcus erythropolis* is used in the method of the invention, then the corresponding (S)-hydroxy compound is obtained from the compound of the formula I. If, for example, an alcohol dehydrogenases of *Lactobacillus* kefir or *Lactobacillus* brevis is used in the method of the invention, then the corresponding (R)-hydroxy compound is obtained from the compound of the formula I.

The alcohol dehydrogenase may be used in the method of the invention either in completely purified or in partially purified form or when inside cells. The cells used here may be in native, permeabilized or lysed form.

The volume activity of the alcohol dehydrogenase used is from 100 units/ml (U/ml) to 2000 U/ml, preferably about 800 U/ml, with a protein content of about 20 mg/ml to 22 mg/ml. The alcohol dehydrogenase preferably used has a specific activity of from about 35 to 40 U/mg of protein. From 20 000 to 200 000 U, preferably about 100 000 U, of alcohol dehydrogenase are used per kg of compound of the formula I to be converted. The enzyme unit 1 U corresponds to the amount of enzyme required in order to convert 1 μmol of the compound of the formula I per minute (min).

The method of the invention is carried out, for example, in a closed reaction vessel made of glass or metal. For this purpose, the components are transferred individually into the reaction vessel and stirred, for example, under a nitrogen or air atmosphere stirring. The reaction time is from 1 day to 14 days, preferably from 4 to 7 days, depending on the substrate and the compound of the formula I used.

The reaction mixture is subsequently worked up. For this purpose, the aqueous phase is removed and the ethyl acetate phase is filtered. The aqueous phase can, optionally, be extracted once more and worked up further like the ethyl acetate phase. This is followed by evaporating the filtered phase under reduced pressure. This results, for example, in the product ethyl 4-chloro-3-(S)-hydroxybutanoate which has an enantiomeric purity of more than 99.9% and is essentially free of the reactant ethyl 4-chloro-3-oxo-butanoate. After distillation of the product, the total yield of the processes is from 82% to 88%, based on the amount of reactant used.

Surprisingly, the organic solvents having a logP of from 0 to 4 demonstrate a stabilizing action on alcohol dehydrogenase, while the prior art advises against the use of the two-phase systems with organic solvents (M. R. Kula, U. Kragel; chapter 28, Dehydrogenases in Synthesis of Chiral Compounds; R. N. Patel, Stereoselective Biocatalyses, 2000; Peters J. 9. Dehydrogenases-Characteristics, Design of Reaction Conditions, and Application, In: H. J. Rehm, G. Reed Biotechnology, Vol. 3, Bioprocessing, VCH Weinheim, 1993; J. Lynda et al., Solvent selection strategies for extractive Biocatalysis, Biotechnol. Prog. 1991, 7, pages 116-124). The organic phase used in the method of the invention is ethyl acetate, said, organic phase serving on the one hand as reservoir for the compound of the formula I but also the reaction product, the chiral hydroxy compound, being simultaneously extracted from the aqueous phase.

In contrast to the prior art, the use of organic solvents having a log-P value of from 0 to 3 results in an additional stabilization of alcohol dehydrogenase, which increases with time. In the prior art, organic solvents having a log-P value (logarithm of the octanol/water distribution coefficient) of from 0 to 2, in particular, have a particularly destabilizing action on enzymes and are thus hardly considered as organic phase in the two-phase system (K. Faber, Biotransformations in organic chemistry, 3$^{rd}$ edition 1997, Springer Verlag, chapter 3. to 3.17).

The invention further relates to *Lactobacillus* minor alcohol dehydrogenase which has a high temperature optimum. *Lactobacillus* minor alcohol dehydrogenase has the DNA sequence according to SEQ ID NO: 3 and the amino acid sequence according to SEQ ID NO: 4 according to the attached sequence protocol. Said *Lactobacillus* minor alcohol dehydrogenase is R-specific, and it is possible, for example, to obtain from a compound of the formula I the corresponding (R)-hydroxy compound. Surprisingly, the enantioselective alcohol dehydrogenase from *Lactobacillus* minor can be overexpressed in *Escherichia coli* RB 791, while alcohol dehydrogenases of other species of the genus *Lactobacillus* were expressed only to a substantially lower extent. This is all the more surprising, since the wild-type strain of *Lactobacillus* minor itself expresses only very small amounts of alcohol dehydrogenase which was therefore not detectable by common screening methods (whole cell biotransformation, activity assay). It was therefore very surprising that it was possible to clone an R-enantioselective alcohol dehydrogenase from *Lactobacillus* minor and to overexpress it in *Escherichia coli* to such an extraordinarily large extent (50% of the cellular proteins of the clone, 20 000 units/g of wet mass).

The purified enzyme from *Lactobacillus* minor is stable in a pH range from about 5.5 to 8.5. The enzyme is stable to about 40° C. and the pH optimum of the enzymic reaction is in the range from pH 7 to pH 7.5. The temperature optimum of the enzymic reaction is about 55° C. The enzyme has a broad spectrum of substrates.

The enzyme can be purified to a specific activity of from 35 to 40 U/mg of protein by means of hydrophobic interaction chromatography.

The invention also relates to a method for obtaining alcohol dehydrogenase from *Lactobacillus* minor. For this purpose, the DNA coding for *Lactobacillus* minor alcohol dehydrogenase is expressed in a suitable prokaryotic or eukaryotic microorganism. *Lactobacillus* minor alcohol dehydrogenase is preferably transformed into and expressed in an *Escherichia coli* strain, in particular in *Escherichia coli* RB 791.

*Lactobacillus* minor alcohol dehydrogenase can be obtained, for example, in such a way that the recombinant *Escherichia coli* cells are cultured, expression of said alcohol dehydrogenase is induced and then, after about 10 to 18 hours (h), the cells are disrupted by ultrasound treatment or by means of a French press (Gaullin, Siemens). The cell extract obtained may either be used directly or be purified further. For this purpose, the cell extract is centrifuged, for example, and the supernatant obtained is subjected to a hydrophobic interaction chromatography. Said chromatography is preferably carried out at pH 7.0 in an aqueous buffer which also contains magnesium ions.

The invention further relates to a method for obtaining an enantioselective (S)-hydroxy compound of the formula II

$$R^1\text{---}C(OH)\text{---}R^2 \qquad (II)$$

where $R^1$ and $R^2$ are, independently of one another, identical or different and are 1. hydrogen,
2. —$(C_1\text{-}C_{20})$-alkyl in which alkyl is straight-chained or branched,
3. —$(C_2\text{-}C_{20})$-alkenyl in which alkenyl is straight-chained or branched and, optionally, comprises one, two, three or four double bonds,
4. —$(C_2\text{-}C_{20})$-alkynyl in which alkynyl is straight-chained or branched and, optionally, comprises one, two, three or four triple bonds,
5. —$(C_6\text{-}C_{14})$-aryl,
6. —$(C_1\text{-}C_8)$-alkyl-$(C_6\text{-}C_{14})$-aryl or
7. $R^1$ and $R^2$ form in combination with the —C(O) radical
   a —$(C_6\text{-}C_{14})$-aryl or a —$(C_6\text{-}C_{14})$-heterocycle,
   where the radicals defined above under 1. to 7. are unsubstituted or, independently of one another, mono- to trisubstituted by
   a) —OH,
   b) halogen such as fluorine, chlorine, bromine or iodine,
   c) —$NO_2$,
   d) —C(O)—O— $(C_1\text{-}C_{20})$-alkyl in which alkyl is linear or branched and unsubstituted or mono- to tri-substituted by halogen, hydroxyl, amino or nitro, or
   e) —$(C_6\text{-}C_{14})$-heterocycle which is unsubstituted or mono- to tri-substituted by halogen, hydroxyl, amino or nitro, characterized in that a) a racemic mixture comprising the compound of the formula II, the alcohol dehydrogenase of the invention, water, cofactor and an organic solvent an organic solvent having a logP of from 0.5 to 4.0, for example from the series diethyl ether, tert-butyl methyl ether, diisopropyl ether or ethyl acetate, is incubated
b) in a two-phase system and
c) the enantiomerically pure (S)-hydroxy compound formed is isolated.

The reaction conditions are essentially the same as in the abovementioned method for the enantiospecific reduction of the keto compound of the formula I. However, instead of enantioselectively reducing the keto compound of the formula I, the method comprises oxidizing the corresponding (R)-hydroxy compound of the formula II to the corresponding keto compound. Furthermore, the method uses acetone rather than isopropanol for regenerating NADP. For example, the alcohol dehydrogenase of the invention converts acetone and NADPH to NADP and isopropanol. The amount of acetone used is from 5% to 30%, based on the volume of the total mixture. Preferred amounts of acetone are from 10% to 20%, in particular 10%.

The alcohol dehydrogenase of the invention may be present for preparation of the compound of the formula II in either completely or partially purified form or may also be used in said method when inside cells. Said cells may be present here in a native, permeabilized or lysed form.

The invention also relates to a recombinant *Escherichia coli* clone, RB 791, which expresses *Lactobacillus* minor alcohol dehydrogenase and which was deposited under the conditions of the Budapest. Treaty with the Deutsche Sammlung für Mikroorganismen und Zellkulturen, Mascheroder Weg 1b, 38124 Brunswick on Mar. 26, 2001 under the number DSM 14196.

The invention is illustrated by the following examples:

EXAMPLE 1

Screening for R-Alcohol Dehydrogenases in Strains of the Genus *Lactobacillus* by Means of Whole Cell Biotransformation Various *Lactobacillus* strains were cultured for screening in the following medium (numbers in each case in g/l): glucose (20), yeast extract (5), meat extract (10), diammonium hydrogen citrate (2), sodium acetate (5), magnesium sulfate (0.2), manganese sulfate (0.05), dipotassium hydrogen phosphate (2).

The medium was sterilized at 121° C. and the strains of the genus *Lactobacillus* (abbreviated to L. hereinbelow) were cultured without further pH regulation or addition of oxygen. The cells were subsequently removed by centrifugation, and in each case 4 g of cells were resuspended for whole cell biotransformation in a final volume of 10 ml of potassium phosphate buffer (KPi buffer) (50 mM, pH=7.0). After addition of in each case 0.1 g of glucose, the cells were shaken at 30° C. for 15 min. Ethyl 4-chloro-3-oxo-butanoate was added at a final concentration of 40 mM to the cell suspension, and the medium was analyzed by gas chromatography in each case after 10 min and 120 min. For this purpose, the cells were removed by centrifugation, the supernatant was filtered and diluted in chloroform to a final concentration of 10-15 µg/ml of ethyl 4-chloro-3-oxobutanoate.

The various *Lactobacillus* strains were used to convert ethyl 4-chloro-3-oxobutanoate, used as substrate, with the following enantiomeric purity to ethyl (S)-4-chloro-3-hydroxybutyrate.

The enantiomeric excess is calculated as follows:

$$ee(\%)=((R\text{-alcohol}-S\text{-alcohol})/(R\text{-alcohol}+S\text{-alcohol}))\times 100.$$

TABLE 1

| *Lactobacillus* strain | ee of ethyl 4-chloro-3-(S)-hydroxybutanoate in % |
|---|---|
| L. reuteri | 34.6 |
| L. kandleri | 90 |
| L. collinoides | 71.3 |
| L. bifermentans | 53.6 |
| L. oris | 63.4 |
| L. brevis | 74 |
| L. halotolerans | 67.2 |
| L. minor | 18.6 |
| L. parabuchneri | 78.5 |
| L. kefir | 87.8 |
| L. fructosus | 28.9 |

EXAMPLE 2

Obtaining Recombinant R-Specific Alcohol Dehydrogenases

A.) Preparation of Genomic DNA from Strains of the Genus *Lactobacillus*

The cell pellet of approximately 2 ml of culture liquid of the genus *Lactobacillus* was resuspended in 300 µl of TE buffer (containing 10 mM Tris/HCl, pH=8.1 mM EDTA), admixed with 20 mg/ml lysozyme and incubated at 37° C. for 10 min. This was followed by adding 100 µl of sodium dodecylsulfate (SDS) (10%), 100 µl of sodium perchlorate (5M) and 500 µl of chloroform/isoamyl alcohol (24:1). After shaking vigorously, the protein was removed by centrifugation and the aqueous phase transferred to a new Eppendorf vessel and this was followed by adding 800 µl of ethanol (EtOH) (96%). The Eppendorf vessel was inverted several times and the precipitated chromosomal DNA then transferred to a new Eppendorf vessel and washed with 200 µl of EtOH. The DNA was again transferred to a new Eppendorf vessel, dried under reduced pressure and dissolved in 100 µl of TE buffer.

B.) Oligonucleotides as 5' and 3' Primers for PCR (Polymerase Chain Reaction)

The primers used for the PCR were derived from the known N-terminal and C-terminal sequence of *L. kefir* alcohol dehydrogenase, with known preferences for particular codons in lactobacilli being taken into account. Thus, the codon ATG (Met) as start codon was put in front of each 5' primer, and furthermore the cleavage site for the restriction enzyme Bam HI (GGATCC) was located upstream of said start codon on the 5' primer, in order to enable subsequent cloning into the expression sector. The stop codon (TAG) and the cleavage site for Hind III (AAGCTT) were placed downstream of the 3' primer. The primer constructs are listed below:

```
N = A, T, C or G; Y = T or C; R = A or G
5' primer
                                    (SEQ ID NO: 1)
5'GCGGATCCATGACNGAYCGNTTRAARGGNAARGTNGC3'

3' primer
                                    (SEQ ID NO: 2)
5'GGGAAGCTTCTAYTGNGCNGTRTANCCNCCRTCNAC3'
```

The primers were prepared according to known methods.

C.) PCR (Polymerase Chain Reaction) with Genomic DNA from Strains of the genus *Lactobacillus*

PCR mixture (100 µl):

| | Amount used per reaction | Concentration |
|---|---|---|
| dNTP's | 8 µl | per NTP 2.5 nmol/µl |
| Oligos | per oligo 10 µl: 20 µl | 2 pmol/µl |
| Chromosomal DNA | 3 µl | ca. 1 µg/µl |
| 10 × buffer (Promega) | 10 µl | |
| Taq polymerase (Promega) | 1 µl | 2 U/µl |
| H$_2$O | 58 µl | | dNTPs are a mixture of deoxynucleotide triphosphates such as dATP, dGTP, dCTP, dTTP Cycle:
95° C. for 2 min, followed by
maintaining 80° C.
  hot start, followed by
95° C. for 30 sec, followed by
40° C. for 1 min 30×
followed by in each case 30 times 95° C. for 30 s and 40° C. for 1 min, then
72° C. for 2.5 min,
followed by
72° C. for 2.5 min
followed by
maintaining 10° C.

For analysis, 10 µl of the mixture were applied to a 1% strength agarose gel and electrophoretically fractionated at a constant 100 V. The PCRA revealed distinct amplification of a DNA piece of approximately 750 bp.

D.) Isolation of PCR Fragments from the Gel

In order to obtain the PCR fragment, the entire PCR mixture was applied to a 1% strength agarose gel and electrophoretically fractionated at a constant 100 V. For this purpose, the gel was divided into two lanes, one containing the complete PCR mixture and the other one containing only a sample of 5 µl, so that the PCR fragment was excised from the gel by staining with ethidium bromide only the lane with the sample for orientation purposes, in order to rule out damage due to ethidium bromide and UV light of the PCR fragment to be isolated.

Isolation from the gel was carried out using the QIAquick Gel Extraction Kit from Qiagen, Hilden, Germany.

A total concentration of 20 ng/µl DNA was determined.

E.) Ligation

To prepare the ligation, the purified PCR fragment and the cloning vector used, pQE30 or pQE70, both from Quiagen, were cleaved with Bam HI and Hind III (4 µl of DNA=200 ng of DNA, 1 µl of 10× buffer, 1 µl of enzyme, BSA and $H_2O$ (Biolabs, New England)).

The cleaved plasmid was then purified again by means of the QIAquick Gel Extraction Kit, taken up in water, dephosphorylated by means of alkaline phosphatase (USB, Amersham Life Science).

For purification, the appropriate reaction mixtures were again applied to a 1% strength agarose gel, and thus the digested amplicon and the plasmid were isolated from the gel, as described under D.). The concentration of plasmid and amplicon after purification was approximately 20 ng/µl.

For ligation, 3 µl of pQE30 or pQE70 (60 ng), 2.5 µl of amplicon (50 ng), 2 µl of ligase buffer (Boehringer; Mannheim), 1.5 µl of $H_2O$ and 1 µl of T4 ligase (Boehringer; Mannheim) were used. The mixture was incubated at 16° C. overnight.

Subsequently, 40 µl of electrocompetent Escherichia coli RB791 cells were transformed with 1.5 µl of ligation mixture by electroporation. The cells were introduced to 500 µl of SOC medium, incubated at 37° C. for 45 min and then in each case 250 µl were plated out on $LB_{amp}$ agar plates. The SOC medium contains per liter of water 20 g of tryptone, 5 g of yeast extract, 0.5 g of NaCl, 10 ml of 1 M $MgSO_4$ and 10 ml of 1 M $MgCl_2$. $LB_{amp}$ agar plates contain per liter of water 10 g of tryptone, 5 g of yeast extract, 10 g of NaCl, 20 g of agar, pH 7.0, and 50 mg of ampicillin.

Grown colonies were removed and cultured in 4 ml of liquid culture ($LB_{amp}$ medium) at 37° C. overnight. In each case 2 ml of this cell suspension were used for plasmid preparation (according to the Quiagen miniprep protocol (Quiagen, Hilden, Germany)).

The plasmid was prepared starting with a Bam HI and Hind III restriction digest. The complete digest was applied to a 1% strength agarose gel and electrophoretically fractionated at 100 V (detection of the 750 kp insert), followed by using the plasmids for sequencing optionally.

Clones having the 750 kp insert were then plated out on $LB_{amp}$ agar plates.

F.) Sequencing of Plasmids

Sequencing was carried out by means of SequiThermEXCEL II Long-Read DNA Sequencing Kit (Biozym, Oldendorf, Germany) on an Li-Cor sequencer (MWG Biotech, Ebersberg, Germany), according to the manufacturer's instructions. The primers used were the standard sequencing primers for pQE vectors.

G.) Screening of Clones with Respect to Soluble R-ADH Expression

Clones having inserts of 750 kp were studied with regard to enzymic activity and stereoselectivity. For this purpose, the clones were removed from the $LB_{amp}$ agar plates and cultured in 20 ml of liquid cultures ($LB_{amp}$ medium) at 25° C. and then, at a cell density ($OD_{500}$) of 0.5, induced with 1 mM isopropyl-β-D-thiogalactopyranoside (IPTG). After 18 h, the cells were removed by centrifugation and in each case 40 mg of cells were taken up in 350 µl of Kpi buffer (50 mM, pH=7, 1 mM $MgCl_2$). The enzyme was liberated from the cells by wet grinding with the aid of glass beads (0.5 g, 0.3 mm). In addition, the cells were disrupted by means of a Retsch mill at 4° C. for 20 minutes.

The enzyme assay contained 870 µl of triethanolamine buffer (100 mM, pH=7.0, 1 mM $MgCl_2$), 100 µl of a 100 mM solution of ethyl 4-chloro-acetoacetate, 10 µl of NADPH (final concentration 0.19 mM), and 20 µl of enzyme solution.

Enzyme unit definition: 1 U corresponds to the amount of enzyme required for converting 1 µmol of substrate (ethyl 4-chloro-3-oxobutanoate) per 1 min.

Stereoselectivity was detected by incubating 480 µl of triethanolamine buffer (100 mM, pH=7.0, 1 mM $MgCl_2$) with 1.0 mM ethyl 4-chloro-3-oxobutanoate, 1.9 mM NADPH (in each case final concentration) and 20 µl of enzyme solution. After incubating for 15 min, the reaction mixture was filtered and diluted 1:10 in chloroform, and a sample was analyzed by means of GC-MS.

Conditions of gas chromatography (GC):
Chiral column: Lipodex E, ID 0.25 mm, 1=25 m (Macherey-Nagel)
1. 2 min 60° C.
2. in 28 min from 60° C. to 130° C. with a rate of 2.5° C. per minute
3. 15 min at 130° C.

An (R)-specific alcohol dehydrogenase was able to be cloned and actively overexpressed from the following Lactobacillus strains:

| Strain | Plasmid | Clone number | Activity in U/g of cells* | ee in % |
|---|---|---|---|---|
| L. parabuchneri | pQE30 | 12 | 450 | >99.9 |
| L. parabuchneri | pQE30 | 14 | 170 | >99.9 |
| L. kandleri | pQE30 | 11 | 280 | >99.9 |
| L. kandleri | pQE70 | 17 | 710 | >99.9 |
| L. minor | pQE30 | 2 | 2 830 | >99.9 |
| L. minor | pQE70 | 3 | 680 | >99.9 |
| L. minor | pQE70 | 4 | 700 | >99.9 |

*Activity calculated from G.) (wet grinding); the activities are considerably higher after fermentation and disruption by French press.

H.) Enzyme Obtainment and Purification

The enzyme was obtained by culturing the strain with the highest enzymic activity in a fermenter (fed batch, 10 l) and inducing it at 40 $OD_{500}$ with 1 mM IPTG. After 18 h, the cells were harvested, taking up 300 g of cells in 3 l of Kpi buffer (50 mM, pH=7, 1 mM $MgCl_2$) and disrupted subsequently by means of a French press (Gaullin, Siemens). The supernatant obtained after centrifugation is referred to as crude extract hereinbelow and had a volume activity of approximately 2000 U/ml (20 000 U/g of wet mass).

To characterize the enzyme, a portion of the enzyme obtained was purified by means of hydrophobic interaction chromatography on Q-Sepharose ff (fast flow). For this purpose, the column used was equilibrated with 50 mM Kpi buffer pH=7.0, 1 mM $MgCl_2$. After application of the crude extract to the column and brief washing with equilibration buffer, the enzyme was eluted with an increasing linear salt gradient (0-1M NaCl, 1 ml/min) at a salt concentration of about 0.3 M NaCl. Combining the enzyme-containing fractions resulted in approximately 25 ml of purified enzyme with a volume activity of about 800 U/ml and a protein content of from 20 to 22 mg/ml. The enzyme purified in this way thus has a specific activity of approximately 35 to 40 U/mg of protein.

All enzymic activities were determined at 25° C. The enzyme activity was calculated as follows:

Calculation: 1 unit=conversion of 1 μmol of substrate per min
Lambert-Beer law
NADPH decrease was monitored at 340 nm (see enzymic assay mixture)=ΔE/min
N=enzyme dilution factor
V=enzyme volume in ml (0.01)
$V_{cuvette}$=cuvette volume=1 ml
d=cuvette light path=1 cm
$e_{NADPH}$ NADPH extinction coefficient=6.22 [$mM^{-1}*cm^{-1}$]
Activity=$(\Delta E/min*N*V_{cuvette})/(e_{NADPH}*V*d)$ Protein determination was carried out according to Bradford (Bio-Rad Laboratories GmbH, Protein Assay).

EXAMPLE 3

Enzyme-Catalyzed Preparation of ethyl (S)-4-chloro-3-hydroxybutyrate

A.) On a 5-Liter Scale

The alcohol dehydrogenase crude extract obtained in Example 2 and the coenzyme NADP were employed in the enzyme-catalyzed synthesis of ethyl (S)-4-chloro-3-hydroxybutyrate from ethyl 4-chloro-3-oxobutanoate. The oxidized coenzyme was continuously regenerated due to the concomitant presence of isopropanol so that the reaction requires only catalytic amounts of coenzyme.

The mixture contained:
2 l of triethanolamine buffer 100 mM pH=7.0, 1 mM $MgCl_2$, 10% glycerol,
400 mg of NADP,
600 ml of isopropanol,
800 ml of ethyl acetate,
600 ml of ethyl 4-chloro-3-oxobutanoate and
approximately 100 000 units of alcohol dehydrogenase.

After 3 days of stirring at room temperature, complete conversion of ethyl 4-chloro-3-oxo-butanoate to ethyl (S)-4-chloro-3-hydroxybutyrate with enantiomeric purity of more than 99.9% was detected by gas chromatography.

After removing the aqueous phase, evaporating the solvent and, optionally, distillation, purified ethyl (S)-4-chloro-3-hydroxybutyrate is obtained with an enantiomeric purity of more than 99.9%.

B.) On a 50 l Scale

The reaction mixture for converting 10 l of ethyl 4-chloro-3-oxo-butanoate is composed as follows:
18 l of triethanolamine buffer 100 mM pH=7.0, 1 mM $MgCl_2$, 10% glycerol,
4 g of NADP,
10 l of isopropanol,
10 l of ethyl acetate,
10 l of ethyl 4-chloro-3-oxo-butanoate and
approximately 2 million units of alcohol dehydrogenase (1.25 l of crude extract).

After 7 days of stirring at room temperature, complete conversion of ethyl 4-chloro-3-oxo-butanoate to ethyl (S)-4-chloro-3-hydroxybutyrate with enantiomeric purity of more than 99.9% was detected by gas chromatography.

EXAMPLE 4

Biochemical Characterization of Cloned Alcohol Dehydrogenase from *Lactobacillus* Minor A.) pH Stability The activity of the enzyme as a function of storage in buffers with different pH values in the range from pH 4 to 11 was studied. For this purpose, various buffers (50 mM) in the range from pH 4 to 11 were prepared and the enzyme purified in Example 2 was diluted 1:100 therein and incubated for 30 min. All buffers contained 1 mM $MgCl_2$. 10 μl of this were then used in the normal enzyme assay (triethanolamine buffer 100 mM pH=7.0, 1 mM $MgCl_2$, 10 mM ethyl 4-chloro-3-oxo-butanoate and 0.19 mM NADPH). The reaction was monitored at 30° C. and 340 nm for 1 min.

The starting value here is the measured value obtained immediately after diluting the enzyme in triethanolamine buffer 50 mM pH=7.0. Under predefined conditions, this value corresponded to a change in extinction of 0.20/min and was set as 100% value, with all subsequent measured values being related to this value.

TABLE 2

| pH | Buffer system | Activity in % (n = 2) | Buffer system | Activity in % (n = 2) |
|---|---|---|---|---|
| 4 | sodium acetate/acetic acid | 87.5 ± 6.5 | | |
| 4.5 | sodium acetate/acetic acid | 94.5 ± 3.0 | | |
| 5 | sodium acetate/acetic acid | 94.5 ± 1.5 | MES/NaOH | 55 ± 5 |
| 5.5 | $KH_2PO_4/K_2PO_4$ | 96 ± 3 | MES/NaOH | 77.1 ± 2.1 |
| 6 | $KH_2PO_4/K_2PO_4$ | 100 ± 0 | triethanol-amine/NaOH | 100 ± 0 |
| 6.5 | $KH_2PO_4/K_2PO_4$ | 97.5 ± 2.5 | triethanol-amine/NaOH | 100 ± 0 |
| 7 | $KH_2PO_4/K_2PO_4$ | 100 ± 0 | triethanol-amine/NaOH | 97.9 ± 2.1 |
| 7.5 | $KH_2PO_4/K_2PO_4$ | 97.5 ± 7.5 | tris/HCl | 94.6 ± 1.3 |
| 8 | $KH_2PO_4/K_2PO_4$ | 93.0 ± 3.0 | tris/HCl | 89.2 ± 0 |
| 8.5 | $KH_2PO_4/K_2PO_4$ | 102.5 ± 2.5 | tris/HCl | 60 ± 4.2 |
| 9 | glycine/NaOH | 76.5 ± 1.5 | tris/HCl | 63.1 ± 4.8 |
| 9.5 | glycine/NaOH | 52.5 ± 7.5 | | |
| 10 | glycine/NaOH | 52.5 ± 7.5 | | |
| 11 | glycine/NaOH | 0.0 ± 0 | | |

Table 2 indicates that the enzyme has good pH stability, in particular in the acidic range, the enzyme stability appearing to be a function not only of the pH but also of the buffer system used. When using, for example, TRIS and MES buffers, the enzyme is found to be inactivated more strongly than in the KPi buffer with the same pH.

There was no significant inactivation in the KPi buffer in the pH range from 5.5 to 8.5.

B.) Temperature Stability

The temperature stability for the range from 25° C. to 50° C. was determined similarly to the manner described in A.). For this purpose, in each case a 1:100 dilution of the purified enzyme was incubated at the particular temperature for 30 min and then measured at 30° C. using the above assay procedure. Here too, the starting value used was the measured value obtained immediately after diluting the enzyme in triethanolamine buffer 50 mM pH=7.0. This value was also set here as 100% value. L. minor alcohol dehydrogenase is stable up to a temperature of 40° C. Thereafter, the activity rapidly declines.

TABLE 3

| Temperature | Activity in % (n = 4) |
|---|---|
| 25 | 101 ± 3.2 |
| 30 | 81.2 ± 5.8 |
| 35 | 67.0 ± 1.6 |
| 37 | 20.2 ± 2.4 |
| 40 | 33.4 ± 3.8 |
| 42 | 0 ± 0 |
| 45 | 0 ± 0 |
| 50 | 0 ± 0 |

C.) pH Optimum

The pH optimum was determined by determining the enzymic reaction in the relevant buffer listed in Table 3. As in the standard assay, the concentration of ethyl 4-chloro-3-oxo-butanoate and of NADPH was 10 mM and 0.19 mM, respectively. The reaction was determined at 30° C. The enzyme of the invention was found to have a pH optimum between 7 and 7.5.

TABLE 4

| pH | Buffer system | Activity in U/ml of undiluted enzyme |
|---|---|---|
| 4 | sodium acetate/acetic acid | 85 |
| 4.5 | sodium acetate/acetic acid | 132 |
| 5 | MES/NaOH | 218 |
| 5.5 | MES/NaOH | 240 |
| 6 | triethanolamine/NaOH | 381 |
| 6.5 | triethanolamine/NaOH | 349 |
| 7 | triethanolamine/NaOH | 510 |
| 7.5 | tris/HCl | 707 |
| 8 | tris/HCl | 585 |
| 8.5 | tris/HCl | 486 |
| 9 | tris/HCl | 488 |
| 10 | glycine/NaOH | 131 |
| 11 | glycine/NaOH | 0 |

D.) Temperature Optimum

The optimal assay temperature was determined by measuring the enzyme activity from 25° C. to 60° C. The assay mixture corresponded to the standard concentration of ethyl 4-chloro-3-oxo-butanoate and NADPH. As Table 5 demonstrates, the optimal assay temperature of the enzyme is 55° C., with the activity declining rapidly thereafter.

TABLE 5

| Temperature | Activity in U/ml of undiluted enzyme |
|---|---|
| 25 | 540 |
| 30 | 1235 |
| 35 | 1968 |
| 40 | 1621 |
| 45 | 2469 |
| 50 | 2469 |
| 55 | 2855 |
| 60 | 0 |

E.) Spectrum of Substrates

Furthermore, substrates other than ethyl 4-chloro-3-oxo-butanoate were also used in the enzymic assay mixture. For this purpose, the following assay mixture was used:

970 µl of triethanolamine buffer (100 mM, pH=7.0, 1 mM MgCl$_2$ containing 10 mM keto compound)
20 µl of NADPH (0.19 mM in assay mixture)
10 µl of enzyme (1:100)

The activity determined with ethyl 4-chloro-3-oxo-butanoate was set to 100% and the enzyme activities of the other substrates were related to this value.

TABLE 6

| Substrate | Activity in % (n = 2) |
|---|---|
| Ethyl 4-chloro-3-oxo-butanoate | 100 |
| Ethyl pyruvate | 192.3 ± 11.5 |
| 2-Octanone | 90.8 ± 1.2 |
| Methyl acetoacetate | 120 ± 7.7 |
| Ethyl 2-oxo-4-phenylbutyrate | 62.7 ± 4.8 |

F.) Enzyme Stability in Organic Solvents

The stability of the enzyme when contacted with organic solvents was studied by diluting L. minor alcohol dehydrogenase 1:100 in the solvent mixtures listed, followed by incubation at room temperature (for organic solvents not miscible with water, the dilution refers to the aqueous phase). Continuous mixing of both phases was ensured (shaker, 200 rpm). 10 µl of the enzyme solution were then used in the standard assay mixture. Here too, the starting value was set to 100% after dilution in the buffer (triethanolamine buffer 100 mM, pH=7.0, 1 mM MgCl$_2$), with all other values being related to this value.

TABLE 7

A.) Water-miscible solvents:

| Solvent | logP | t = 2 h | t = 8 h | t = 24 h | t = 48 h |
|---|---|---|---|---|---|
| Buffer | | 86 | 70 | 3 | 0 |
| 10% isopropanol | 0.28 | 32 | 34 | 16 | 0 |
| 20% isopropanol | 0.28 | 16 | 17 | 7 | 0 |
| 10% DMSO | −1.3 | 73 | 54 | 60 | 40 |
| 20% DMSO | −1.3 | 73 | 54 | 57 | 40 |
| 1M sorbitol | | 93 | 74 | 60 | 6 |
| 10% glycerol | −3 | 120 | 64 | 62 | 28 |
| 20% glycerol | −3 | 120 | 100 | 100 | 104 |

As Table 7A demonstrates, glycerol, DMSO and sorbitol have an activating and, respectively, stabilizing action on the alcohol dehydrogenase used. In contrast, the isopropanol to be used in the process has an inactivating action.

B.) Solvents not miscible with water

| Solvent | logP | t = 2 h | t = 8 h | t = 24 h | t = 48 h |
|---|---|---|---|---|---|
| Buffer | | 86 | 70 | 3 | 0 |
| 20% ethyl acetate | 0.68 | 87 | 50 | 10 | 8 |
| 20% diethyl ether | 0.85 | 53 | 42 | 37 | 23 |
| 20% tert-butyl methyl ether | 1.21 | 67 | 51 | 38 | 24 |
| 20 diisopropyl ether | 1.55 | 100 | 57 | 41 | 29 |
| 20% dibutyl ether | 2.9 | 92 | 71 | 23 | 6 |
| 20% pentane | 3 | 74 | 55 | 7 | 6 |
| 20% hexane | 3.5 | 80 | 39 | 2 | 5 |
| 20% heptane | 4 | 51 | 49 | 7 | 6 |
| 20% octane | 4.5 | 87 | 47 | 2 | 1 |

As Table 7B demonstrates, the alcohol dehydrogenase studied exhibits considerable stability in a large number of organic solvents. Surprisingly, solvents having logP values between 0 and 3 inhibit the alcohol dehydrogenase studied no more than those having logP values between 3 and 4.5, in particular with regard to longer incubation times (24 h and 48 h) solvents having logP values between 0 and 3 stabilize the ADH studied, compared to the corresponding values in the buffer. The aliphatic solvents studied, pentane, hexane, heptane and octane, do not exhibit this stabilizing action with long-term incubation.

The logP value of a component X is the logarithm of the distribution coefficient of X in the octanol/water two-phase system (50/50)
P=concentration of X in octanol phase/concentration of X in aqueous phase G. Enzyme Stability Under Process Conditions The stability of the enzyme under process conditions was studied by diluting L. minor alcohol dehydrogenase 1:100 with the solvent mixtures used in the two-phase system, followed by incubation at room temperature. 10 μl of the enzyme solution were then used in the standard assay mixture.

Table 8 depicts the enzyme activities as a % of the starting value.

TABLE 8

|  | 6 h | 20 h | 46 h | 60 h | 84 h |
|---|---|---|---|---|---|
| Triethanolamine buffer, 100 mM, 1 mM MgCl$_2$ | 100 | 75 | 0 | 0 | 0 |
| Mixture B | 100 | 85 | 80 | 60 | 55 |
| Mixture C | 110 | 95 | 95 | 85 | 80 |
| Mixture D | 100 | 65 | 55 | 50 | 50 |

Mixture B: buffer, 10% glycerol, 10% isopropanol
Mixture C: buffer, 20% glycerol, 20% isopropanol
Mixture D: buffer, 10% glycerol, 10% isopropanol + 20% ethyl acetate It was found that recombinant L. minor alcohol dehydrogenase is stable and active in the combination of solvents used in the two-phase system for several days.

The invention claimed is:

1. A method for the enantioselective reduction of a keto compound of the formula I

$$R^1\text{—}C(O)\text{—}R^2 \qquad (I)$$

where $R^1$ and $R^2$ are, independently of one another, identical or different and are
(i) a hydrogen atom;
(ii) —$(C_1\text{-}C_{20})$-alkyl in which alkyl is straight-chained or branched;
(iii) —$(C_2\text{-}C_{20})$-alkenyl in which alkenyl is straight-chained or branched and, optionally, comprises one, two, three or four double bonds;
(iv) —$(C_2\text{-}C_{20})$-alkynyl in which alkynyl is straight-chained or branched and, optionally, comprises one, two, three or four triple bonds;
(v) —$(C_6\text{-}C_{14})$-aryl;
(vi) —$(C_1\text{-}C_8)$-alkyl-$(C_6\text{-}C_{14})$-aryl or
(vii) $R^1$ and $R^2$ form in combination with the —C(O) radical a —$(C_6\text{-}C_{14})$-aryl or a —$(C_5\text{-}C_{14})$-heterocycle,
where the radicals defined above under (i) to (vii) are unsubstituted or, independently of one another, mono- to trisubstituted by
—OH;
halogen;
—$NO_2$;
—C(O)—O—$(C_1\text{-}C_{20})$-alkyl in which alkyl is linear or branched and unsubstituted or mono- to trisubstituted by halogen, hydroxyl, amino or nitro, or
—$(C_5\text{-}C_{14})$-heterocycle which is unsubstituted or mono- to trisubstituted by halogen, hydroxyl, amino or nitro,
said method comprising
(a) admixing a reaction batch comprising a compound of the formula (I) in a proportion of from 10% to 25%, based on the total volume of the reaction batch, with alcohol dehydrogenase, water, cofactor NADPH or NADH and an organic solvent having a logP of from 0.6 to 3.0;
(b) incubating a two-phase system of water, organic solvent and the compound of formula (I) to produce a chiral hydroxyl compound and oxidized cofactor;
(c) continuously regenerating cofactor from oxidized cofactor produced by said alcohol dehydrogenase, and
(d) isolating the chiral hydroxy compound.

2. The method as claimed in claim 1, wherein the compound of the formula (I) is selected from 4-chloro-3-oxobutanoic acid ethyl ester, acetophenone, methyl acetoacetate, ethyl 2-oxo-4-phenylbutyrate, 2,5-hexanedione, ethyl pyruvate or 2-octanone.

3. The method as claimed in claim 1, wherein the organic solvent has a logP of from 0.63 to 1.75.

4. The method as claimed in claim 1, wherein the organic solvent is diethyl ether, tert-butyl methyl ether, diisopropyl ether or ethyl acetate.

5. The method as claimed in claim 1, wherein the alcohol dehydrogenase is derived from yeast, horse liver, *Thermoanaerobium brockii, Rhodococcus erythropolis, Latobacillus kefir, Lactobacillus brevis, Lactobacillus* minor or is an alcohol dehydrogenase having the amino acid sequence according to SEQ ID NO. 4.

6. The method as claimed in claim 5, wherein the alcohol dehydrogenase is present in an amount of from 20 000 U to 200 000 U per kg of compound of the formula (I) to be reacted.

7. The method as claimed in claim 1, wherein said method further comprises adding a buffer having a pH of from 5 to 10.

8. The method as claimed in claim 7, wherein the buffer is selected from potassium phosphate, Tris/HCl or triethanolamine buffer.

9. The method as claimed in claim 1, wherein said method further comprises adding magnesium ions at a concentration of from 0.2 mM to 10 mM to the buffer.

10. The method as claimed in claim 1, wherein the cofactor is NADPH or NADH, present in an amount of from 0.05 mM to 0.25 mM, based on the aqueous phase.

11. The method as claimed in claim 1, wherein said method further comprises adding glycerol, sorbitol or dimethyl sulfoxide as a stabilizer for the alcohol dehydrogenase.

12. The method as claimed in claim 11, wherein the stabilizer is present in an amount of from 5% to 30%, based on the volume of the total reaction batch.

13. The method as claimed in claim 12, wherein the stabilizer is present in an amount of from 10% to 20%, based on the volume of the total reaction batch.

14. The method as claimed in claim 1, wherein said continuously regenerating step comprises adding isopropanol.

15. The method as claimed in claim 14, wherein the isopropanol is present in an amount of from 5% to 30%, based on the volume of the total reaction batch.

16. The method as claimed in claim 15, wherein isopropanol is present in an amount of from 10% to 20%, based on the volume of the total reaction batch.

17. The method as claimed in claim 1, wherein the compounds of the formula (I) are present in an amount of from 15% to 22% based on the total volume.

18. The method as claimed in claim 1, wherein the reaction batch is at a temperature of from about 10° C. to 70° C.

19. The method as claimed in claim 1, wherein the organic solvent is present in an amount of from 1% to 90%, based on the total volume of the reaction batch.

20. The method as claimed in claim 19, wherein the organic solvent is present in an amount of from 15% to 60%, based on the total volume of the reaction batch.

21. The method as claimed in claim 1, wherein the ratio of organic solvent to water is from 9 to 1 to 1 to 9.

22. A method as claimed in claim 1, wherein the halogen is fluorine, chlorine, bromine or iodine.

* * * * *